United States Patent [19]
Bezwada et al.

[11] Patent Number: 5,037,950
[45] Date of Patent: Aug. 6, 1991

[54] BIOABSORBABLE COPOLYMERS OF POLYALKYLENE CARBONATE/RHO-DIOXANONE FOR SUTURES AND COATINGS

[75] Inventors: Rao S. Bezwada, Whitehouse Station; Shalaby W. Shalaby, Lebanon; Alastair W. Hunter, Bridgewater, all of N.J.

[73] Assignee: Ethicon, Inc., Somerville, N.J.

[21] Appl. No.: 478,300

[22] Filed: Feb. 9, 1990

[51] Int. Cl.$^5$ .................... G08G 63/06; G08G 63/64; A61B 17/04
[52] U.S. Cl. .................................. 528/354; 606/77; 606/154; 606/230
[58] Field of Search ............... 528/354; 606/77, 154, 606/230

[56] References Cited

U.S. PATENT DOCUMENTS

| | | | |
|---|---|---|---|
| 4,440,789 | 4/1984 | Mattei et al. | 528/354 X |
| 4,591,630 | 5/1986 | Gertzman et al. | 528/354 X |
| 4,633,873 | 1/1987 | Dumican et al. | 606/151 |
| 4,643,191 | 2/1987 | Bezwada et al. | 528/354 X |
| 4,652,264 | 3/1987 | Dumican | 623/1 |
| 4,653,497 | 3/1986 | Bezwada et al. | 528/354 X |
| 4,705,820 | 11/1987 | Wang et al. | 528/354 X |
| 4,711,241 | 12/1987 | Lehmann | 606/230 |
| 4,716,203 | 12/1987 | Casey et al. | 525/408 |
| 4,788,979 | 12/1988 | Jarrett et al. | 528/254 X |
| 4,791,929 | 12/1988 | Jarrett et al. | 528/354 X |
| 4,792,336 | 12/1988 | Hlavacek et al. | 623/13 |
| 4,838,267 | 6/1989 | Jamiolkowski et al. | 528/354 X |
| 4,857,602 | 8/1989 | Casey et al. | 525/408 |
| 4,870,966 | 10/1989 | Dellon et al. | 606/152 |
| 4,871,365 | 10/1989 | Dumican | 623/11 |
| 4,891,263 | 2/1990 | Kotliar et al. | 528/354 X |
| 4,916,193 | 4/1990 | Tang et al. | 525/413 |
| 4,965,300 | 10/1990 | Eichenauer et al. | 528/354 X |

Primary Examiner—Earl Nielsen

[57] ABSTRACT

Bioabsorbable copolymers comprising p-dioxanone and AA-BB type polyalkylene carbonates are provided. The copolymers are useful in the fabrication of sterile surgical articles and bioabsorbable coatings for sutures and are produced from organic carbonates by way of prepolymeric synthetic intermediates.

11 Claims, No Drawings

BIOABSORBABLE COPOLYMERS OF POLYALKYLENE CARBONATE/RHO-DIOXANONE FOR SUTURES AND COATINGS

This invention relates to bioabsorbable copolymers, sterile surgical articles fabricated from bioabsorbable copolymers and, more particularly, to coatings for surgical sutures prepared from low molecular weight bioabsorbable copolymers of p-dioxanone and polyalkylene carbonates such as polyhexamethylene carbonate.

The synthesis of copolymers comprising cyclic alkylene carbonates and cyclic esters is well-known in the art. The properties of such copolymers are highly dependent upon the quantity and nature of their respective constituent monomers. Thus, by varying monomers, one can effectively modify the properties of a copolymer comprising alkyl carbonates as appropriate for a given application.

It is well known, for example, to use copolymers of certain cyclic alkylene carbonates and cyclic esters in fabricating sterile surgical articles, such as sutures employed to close wounds or otherwise bind tissue in humans or animals. The utility of such copolymers in the fabrication of sutures derives in large part from the copolymers' unique properties. Certain synthetic copolymers of cyclic alkylene carbonates and cyclic esters can be drawn, extruded, or otherwise shaped into thread-like strands having both relatively high tensile strength and sufficient flexibility for surgical manipulations. Under conditions such as found in the human body, however, many such copolymers hydrolyze or otherwise degrade into chemical fragments which are safely absorbed by the body. Materials which degrade in this manner are commonly known in the art as absorbable or bioabsorbable. Ideally, a bioabsorbable suture should retain its structural integrity for an interval slightly greater than that required for bound bodily tissue to at least partially heal. The suture should then completely absorb to permit full healing.

Synthetic bioabsorbable sutures have gained wide acceptance in the surgical field and are commonly of two configurations: monofilament and multifilament. Monofilament sutures comprise a single thread-like strand, while multifilament sutures may exist in the form of a braid or a twisted yarn of a number of strands. Monofilament constructions are considered more suitable than multifilament or braided configurations for many surgical uses, as they tend to produce less infection and trauma at the wound closure site. But because monofilament sutures tend to be rather stiff, synthetic sutures are usually provided in multifilament form.

Multifilament sutures, however, often possess somewhat rough outer surfaces, resulting in poor knot tiedown performance. Poor knot tiedown performance is manifested, for example, by fibrillation in forming surgical knots with synthetic sutures. Rough suture surfaces may also tend to irritate sensitive bodily tissues such as contacted in the course of surgery. Such contact, which is known in the art as tissue drag, ideally should be minimized.

Thus, because both monofilament and multifilament synthetic sutures having suitable tensile strengths for surgical applications tend to be somewhat more difficult to handle than "natural" sutures made, for example, from catgut, a variety of coatings are often applied to relatively hard and rough synthetic sutures to yield strong sutures having improved handling properties. Calcium stearate is one such coating. U.S Pat. Nos. 4,027,676 and 3,942,532 disclose other coatings which improve the handling properties of sutures, as well as techniques for their application.

Copolymers comprising certain cyclic alkylene carbonates are known to be useful in bioabsorbable coatings for sutures and in the fabrication of numerous other surgical articles. For example, U.S. Pat. Nos. 4,871,365, 4,870,966, 4,857,602, 4,792,336, 4,716,203, 4,711,241, 4,705,820, 4,652,264, and 4,633,873 disclose bioabsorbable coatings for sutures and other surgical articles comprising apparently random copolymers having linkages which correspond to trimethylene carbonate and either glycolic esters or caprolactone. U.S. Pat. No. 4,791,929 discloses bioabsorbable coatings comprising caprolactone copolymers of trimethylene carbonate and ε-caprolactone. U.S. Pat. No. 4,788,979 discloses block copolymers of trimethylene carbonate and caprolactone. Published International Application WO 89/05664 discloses medical devices fabricated from homopolymers and copolymers of cyclic carbonates, such as trimethylene carbonate and derivatives thereof.

Thus, it may be seen that considerable effort has been devoted to obtaining copolymers comprising cyclic carbonates and specifically trimethylene carbonate which are useful in the fabrication of surgical articles, such as bioabsorbable coatings for sutures.

SUMMARY OF THE INVENTION

It is an object of the present invention to produce novel copolymers having improved properties. It is another object of the present invention to produce such novel copolymers which are bioabsorbable. It is yet another object of the present invention to produce bioabsorbable copolymers useful in the fabrication of sterile surgical articles, such as in coatings for sutures. It is still another object of the present invention to produce sutures having good handling properties. It is a further object of the present invention to produce sutures having both good bioabsorbability and good handling properties.

Accordingly, this invention provide bioabsorbable copolymers of p-dioxanone and AA-BB type polyalkylene carbonates, such as polyhexamethylene carbonate. Such copolymers are useful in the fabrication of surgical articles, particularly in bioabsorbable coatings for sutures.

DESCRIPTION OF THE PREFERRED EMBODIMENTS

The bioabsorbable copolymers of this invention comprise sequential units, or linkages, having formulas (I) and (II) where x=4–12, inclusive, preferably 6.

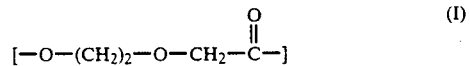

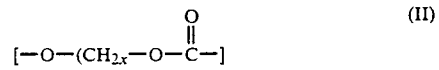

Those skilled in the art will recognize that the repeating units of formula (I) correspond to the repeating monomer units of a polymer of p-dioxanone (PDO; 1,4-dioxan-2-one) and that the repeating units of formula (II) correspond to the repeating monomer units of a polymer of a polyalkylene carbonate. Where x=6, formula (II) corresponds to the repeating monomer units of hexamethylene carbonate, which is preferred.

It is preferred that formula (I) linkages comprise greater than about 51 mole percent of the linkages in copolymers of this invention. It is even more preferred that formula (I) linkages comprise between about 65 to about 90 mole percent, particularly about 80 mole percent.

It is preferred that the copolymers of this invention have relatively low molecular weight for use as coatings. The measurement of inherent viscosity provides one means of determining the magnitude of a polymer's molecular weight; low inherent viscosity corresponds to low molecular weight. The coating copolymers of this invention preferably have inherent viscosities between about 0.1 and about 1.0 deciliters per gram (dl/g) measured at 25° C. in a 0.1 g/dl solution of hexafluoroisopropyl alcohol. It is preferred that such coating polymers have inherent viscosities of between about 0.3 and about 0.5 dl/g.

Since the coating copolymers of this invention have low molecular weights, they tend to be very soft, pliable materials which can be applied as, for example, a coating for bioabsorbable sutures. These copolymers generally penetrate deep into a substrate upon which they might be coated and, consequently, leave less coating build-up on the substrate's surface. For coated sutures, such build-up is manifested by flaking which occurs when the suture is tied into a knot or otherwise bent.

Thus, when sutures are coated with the copolymers of this invention, flaking is reduced.

Because the low molecular weight copolymers of this invention penetrate into a suture, the bioabsorbable coatings exhibit enhanced conformability. Additionally, the copolymers of this invention impart tactile smoothness to surgical articles upon which they might be coated. Such smoothness serves, for example, to reduce the tissue drag of sterile sutures. As will be recognized by those skilled in the art, lower molecular weight coating copolymers also lessen the degree of fibrillation during the formation of both wet and dry knots. In addition to imparting improved handling properties to sutures, the low molecular weight copolymers of this invention are more readily absorbed into bodily tissues than higher molecular weight polymers.

The copolymers of this invention may exist as a single copolymer or as a mixture of copolymers. It will be recognized by those of skill in the art that it is possible to produce a wide variety of mixtures of copolymers synthesized in accordance with this invention. In many applications, copolymeric materials comprising a mixture of copolymers of this invention exhibit properties, such as inherent viscosity, which correspond to those of a single copolymer. Such copolymeric materials are intended to be within the scope of the present invention.

The copolymers of this invention find many applications and may be a sole or partial component of shaped bodies or other articles of manufacture. For example, this invention provides improved sterile surgical articles, particularly sutures, which comprise bioabsorbable copolymers of PDO and polyalkylene carbonates. The copolymers of this invention may be extruded and drawn to prepare monofilament or multifilament sutures which can be, if desired, attached to one or more needles, or they may be coated upon sutures as solutions in organic solvents. In preferred embodiments, coatings comprising low molecular weight bioabsorbable copolymers are applied to bioabsorbable multifilament sutures to improve the handling properties thereof. Such coatings comprise between about 2 and about 15 weight percent of a bioabsorbable suture. It is preferred that such coatings comprise between about 3 and about 10 weight percent of a bioabsorbable suture. Those skilled in the art will recognize that the appropriate amount of coating applied to a suture varies with the suture's size, with smaller sutures requiring lower weight percent coating.

The copolymers of this invention can be synthesized from certain organic carbonate moieties through processes which involve the formation of prepolymer intermediates. In accordance with this invention, a prepolymer of a diol and organic carbonate monomers is formed using a suitable catalyst. Representative diols include 1,6-hexanediol, 1,4-butanediol and 1,8-octanediol; representative organic carbonates include diphenyl carbonate and dibutyl carbonate. In preferred embodiments hexanediol, carbonate and stannous octoate catalyst to form prepolymers of polyhexamethylene carbonate. The prepolymers of this invention should comprise from about 0.5 to about 0.6 mole percent diol and from about 0.4 to about 0.5 mole organic carbonate. It is preferred that the prepolymers of this invention comprise from about 0.50 to about 0.55 mole percent diol and from about 0.45 to about 0.50 mole percent organic carbonate. Those skilled in the art will appreciate that the molecular weights of prepolymers can be controlled by a variety of techniques, such as by varying the rates of the respective reactants and reaction conditions.

Once a prepolymer such as polyhexamethylene carbonate is formed, PDO is added thereto. Copolymerization of PDO and the prepolymer to form bioabsorbable copolymers of this invention ensues and, indeed, is initiated by the prepolymer. Thus, it can be seen that the molecular weight of a bioabsorbable copolymer according to this invention depends upon the molecular weight of the particular prepolymer employed in its synthesis. Low molecular weight prepolymers will yield low molecular weight bioabsorbable copolymers and high molecular weight prepolymers will yield high molecular weight bioabsorbable copolymers and, additionally, the ratio of reactants will also control the molecular weight of the copolymer.

The invention will now be further described in connection with the following examples. Parts and percents are by weight unless otherwise specified. Inherent viscosity was measured at 25° C. in a 0.1 g/dl solution of hexafluoroisopropyl alcohol (HFIP).

EXAMPLE 1

Synthesis and Characterization of Polyhexamethylene Carbonate

A flame dried 250 ml single neck flask is charged with 36.6 g of 1,6 hexanediol and 69.2 g of diphenyl carbonate. The flask is fitted with a mechanical stirrer and an adapter and receiver. The reaction flask is held under vacuum at room temperature for about 18 hours. The reaction is then conducted under nitrogen at 180° C. for 1.5 hours, at 200° C. for 1 hour and then at 220° C. for 3 hours, and then cooled to room temperature. Under high vacuum (0.1 mm Hg) the reaction flask is gradually heated to 200° C. and maintained there for about 18 hours. The resulting polyhexamethylene carbonate is isolated, ground, dried under vacuum (0.1 mm Hg). The polymer has an I.V. of 0.38 dl/g.

EXAMPLE 2

Synthesis and Characterization of Polyhexamethylene Carbonate/Para-Dioxanone Copolymer A flame dried 100 ml single neck flask is charged with 5 g of the polyhexamethylene carbonate of Example 1, and dried at
60° C. and 0.1 mm Hg for 24 hours. Under nitrogen, 20 g (0.196 mole) of p-dioxanone and 0.02 ml of stannous octoate (0.33 molar in toluene) are added to the flask, which is then fitted with a flame dried mechanical stirrer and an adapter. The reaction flask is held under high vacuum (0.1 mm Hg) at room temperature for about 24 hours. The reaction is then conducted in an oil bath at 110° C. for 8 hours under nitrogen. The copolymer is isolated ground, dried at 80° C. under high vacuum to remove any unreacted monomer. The copolymer has an I.V. of 0.38 dl/g.

EXAMPLE 3

Synthesis and Characterization of Polyhexamethylene Carbonate

A flame dried 250 ml single neck flask is charged with 109.8 g (0.929 moles) of 1,6 hexanediol and 192.6 g (0.900 moles) of diphenyl carbonate. The flask is fitted with a mechanical stirrer and an adapter receiver. The reaction flask is held under vacuum at room temperature for about 18 hours. The reaction is then conducted under nitrogen at 180° C. for 1.5 hours, at 200° C. for 1 hour and then at 220° C. for 3 hours, and then cooled to room temperature. Under high vacuum (0.1 mm Hg) the reaction flask is gradually heated to 200° C. and maintained there for about 18 hours, and then heated to 210° C. for 6 hours. The resulting polyhexamethylene carbonate is isolated, ground, dried under vacuum (0.1 mm Hg). The polymer had an I.V. of 1.52 dl/g and a melting range of 54°–65° C. by hot stage microscopy.

EXAMPLE 4

Synthesis and Characterization of Polyhexamethylene Carbonate/Para-Dioxanone Copolymer A flame dried 100 ml single neck flask is charged with 5 g of the polyhexamethylene carbonate of Example 3 and dried at 60° C. and 0.1 mm Hg for 24 hours. Under nitrogen, 20 g (0.196 mole) of p-dioxanone and 0.02 ml of stannous octoate (0.33 molar in toluene) was added to the flask, which is then fitted with a flame dried mechanical stirrer and an adapter. The reaction flask is held under high vacuum (0.1 mm Hg) at room temperature for about 24 hours. The reaction is then conducted in an oil bath at 110° C. for 8 hours under nitrogen. The copolymer is isolated, dried at 80° C. under high vacuum to remove any unreacted monomer. The copolymer has an I.V. of 1.89 dl/g.

EXAMPLE 5

Synthesis and Characterization of Polyhexamethylene Carbonate

A flame dried 250 ml single neck flask is charged with 36.6 g of 1,6 hexanediol and 69.2 g of diphenyl carbonate. The flask is fitted with a mechanical stirrer and an adapter receiver. The reaction flask is held under vacuum at room temperature for about 18 hours. The reaction is then conducted under nitrogen at 180° C. for 1.5 hours, at 200° C. for 1 hour and then at 220° C. for 3 hours, and then cooled to room temperature. Under high vacuum (0.1 mm Hg) the reaction flask is gradually heated to 190° C. and held there for 1.5 hours, at 200° C. for 1 hour and then at 210° C. for 1 hour, and then cooled to room temperature. The resulting polyhexamethylene carbonate is isolated, ground, dried under vacuum (0.1 mm Hg). The polymer has an I.V. of 0.18 dl/g.

EXAMPLE 6

Synthesis and Characterization of Polyhexamethylene Carbonate/Para-Dioxanone Copolymer A flame dried 100 ml single neck flask is charged with 10 g of the polyhexamethylene carbonate of Example 5 and dried at 60° C. and 0.1 mm Hg for 24 hours. Under nitrogen, 40 g (0.3918 mole) of p-dioxanone and 0.04 ml of stannous octoate (0.33 molar in toluene) was added to the flask, which is then fitted with a flame dried mechanical stirrer and an adapter. The reaction flask is held under high vacuum (0.1 mm Hg) at room temperature for about 24 hours. The reaction is then conducted in an oil bath at 110° C. for 8 hours under nitrogen. The copolymer is isolated ground, dried at 80° C. under high vacuum to remove any unreacted monomer. Copolymer conversion is 79%. The copolymer has an I.V. of 1.39 dl/g and a melting range of 104°–106° C. by hot stage microscopy. Composition of polyhexamethylene carbonate/PDO by NMR is found to be 18.7/81.3 mole percent.

EXAMPLE 7

Synthesis and Characterization of Polytetramethylene Carbonate

A flame dried 250 ml single neck flask is charged with 46.86 g (0.52 mole) of 1,4 butanediol and 107.6 g (0.5 moles) of diphenyl carbonate. The flask is fitted with a mechanical stirrer and an adapter receiver. The reaction flask is held under vacuum at room temperature for about 18 hours. The reaction is then conducted under nitrogen at 180° C. for 1.5 hours, at 200° C. for 1 hour and then at 220° C. for 3 hours, and then cooled to room temperature. Under high vacuum (0.1 mm Hg) the reaction flask is gradually heated to 200° C. and maintained there for about 18 hours. The resulting polyhexamethylene carbonate is isolated, ground, dried under vacuum (0.1 mm Hg). The polymer has an I.V. of 0.38 dl/g.

EXAMPLE 8

Synthesis and Characterization of Polytetramethylene Carbonate/Parp-Dioxanone Copolymer A flame dried 100 ml single neck flask is charged with 5 g of the polytetramethylene carbonate of Example 7, and dried at 60° C. and 0.1 mm Hg for 24 hours. Under nitrogen, 20 g (0.196 mole) of p-dioxanone and 0 02 ml of stannous octoate (0.33 molar in toluene) was added to the flask, which is then fitted with a flame dried mechanical stirrer and an adapter. The reaction flask is held under high vacuum (0.1 mm Hg) at room temperature for about 24 hours. The reaction is then conducted in an oil bath at 110° C. for 8 hours and at 90° C. for 18 hours under nitrogen. The copolymer is isolated ground, dried at 80° C. under high vacuum to remove any unreacted monomer. The copolymer has an I.V. of 0.78 dl/g.

EXAMPLE 9

Preparation and Characterization of Monofilament Sutures

The polymers described in Examples 3 and 6, were extruded into monofilament fibers 9A and 9B, respectively, using conventional extrusion techniques. The orientation conditions were as follows:

|  | Stage 1 | Stage 2 | Total Draw Ratio |
| --- | --- | --- | --- |
| 9A | 5x at 41° C. | 1.35x at 60° C. | 6.75x |
| 9B | 4x at 55° C. | 1.375x at 76° C. | 5.5x |

The oriented fiber properties of these samples are summarized below:

|  | 9A | 9B |
| --- | --- | --- |
| Diameter (mils) | 6.9 | 8.2 |
| Tensile Strength, Kpsi | 55 | 58 |
| Knot strength, Kpsi | 38 | 45 |
| Elongation at break | 41% | 58% |
| Youngs modulus, Kpsi | 197 | 137 |

The copolymers of Examples 2, 4, 5, 7 and 8 are applied from solution onto an absorbable multifilament braid prepared from a copolymer of glactide and lactide. The subjective evaluations of suture performance, including dry and wet tie-down properties, pliability and surface asthetics show improvement relative to the performance of an uncoated multifilament braid.

Many different embodiments of this invention will be apparent to those skilled in the art and may be made without departing from its spirit and scope. Thus, it will be understood that this invention is not limited to the specific embodiments thereof.

We claim:

1. A bioabsorbable copolymer comprising from about 51 to about 99 mole percent of sequential units having formula (I);

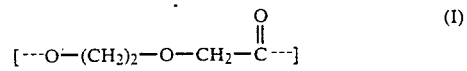

and from about 49 to about 1 mole percent of sequential units having formula (II), wherein x is an integer between 4 and 12, inclusive

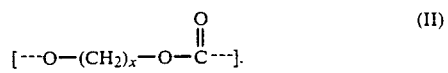

2. The bioabsorbable copolymer of claim 1 wherein x is 6.

3. The bioabsorbable copolymer of claim 2 wherein:
from about 90 to about 65 mole percent of sequential units have formula (I); and
from about 10 to about 35 mole percent of sequential units have formula (II).

4. A sterile surgical article fabricated from the bioabsorbable copolymer of claim 1.

5. A coating for a sterile surgical article comprising the bioabsorbable copolymer of claim 3.

6. The sterile surgical article of claim 5 in the form of a suture.

7. The sterile surgical suture of claim 6 wherein the suture is a monofilament or multifilament suture with or without a needle.

8. A coating for a sterile surgical suture comprising the bioabsorbable copolymer of claim 1.

9. The coating of claim 8 wherein the copolymer has an inherent viscosity between about 0.1 and about 1.0 deciliters per gram measured at 25° C. in a 0.1 dl/g solution of hexafluoroisopropyl alcohol solution.

10. The coating of claim 9 wherein the copolymer is between about 2 and about 15 weight percent of said suture.

11. The coating of claim 10 wherein the copolymer is between about 3 and about 10 weight percent of said suture.

* * * * *

UNITED STATES PATENT AND TRADEMARK OFFICE
CERTIFICATE OF CORRECTION

PATENT NO. : 5,037,950

DATED : August 6, 1991

INVENTOR(S) : Rao S. Bezwada; Shalaby W. Shalaby and Alastair W. Hunter

It is certified that error appears in the above-identified patent and that said Letters Patent is hereby corrected as shown below: Title page:

Item (54), and column 1, lines 1-4 should read--

Bioabsorbable Copolymers of Polyalkylene Carbonate/p-dioxanone for Sutures and Coatings --.

NOT:

Bioabsorbable Copolymers of Polyalkylene Carbonate/RHO-dioxanone for Sutures and Coatings Signed and Sealed this Twelfth Day of January, 1993

Attest:

DOUGLAS B. COMER

Attesting Officer

Acting Commissioner of Patents and Trademarks